United States Patent [19]

Starks et al.

[11] 4,105,698

[45] Aug. 8, 1978

[54] PREPARATION OF CINNAMYL-SUBSTITUTED PHENOLS

[75] Inventors: Charles M. Starks; Allan J. Lundeen, both of Ponca City, Okla.

[73] Assignee: Continental Oil Company, Ponca City, Okla.

[21] Appl. No.: 769,080

[22] Filed: Feb. 16, 1977

[51] Int. Cl.² ............................................. C07C 39/17
[52] U.S. Cl. .................................................... 568/744
[58] Field of Search .................................. 260/619 R

[56] References Cited

U.S. PATENT DOCUMENTS

| | | | |
|---|---|---|---|
| 2,140,782 | 12/1938 | Arnold et al. | 260/619 R |
| 2,678,951 | 5/1954 | Smith et al. | 260/619 R |
| 3,290,389 | 12/1966 | Hahn | 260/619 R |

*Primary Examiner*—Joseph E. Evans
*Attorney, Agent, or Firm*—Bayless E. Rutherford, Jr.

[57] ABSTRACT

A process for preparing ortho-substituted cinnamyl phenols is disclosed. The process comprises heating a mixture of cinnamyl alcohol and phenol in the presence of an effective amount of activated alumina.

8 Claims, No Drawings

PREPARATION OF CINNAMYL-SUBSTITUTED PHENOLS

GENERAL BACKGROUND

Cinnamyl-substituted phenols are useful as biocidal agents.

Methods for the preparation of cinnamyl-substituted phenols are very limited because of the double bond in the cinnamyl substituent, which, under acidic conditions, tends to undergo further alkylation reactions. For example, in the reaction of cinnamyl chloride with phenol, catalyzed by aluminum chloride, only a small yield of cinnamyl phenol is obtained because of several side reactions.

We have discovered a method of preparing cinnamyl-substituted phenols wherein the reaction product contains little, if any, products resulting from alkylation at the double bond.

PRIOR ART

The most pertinent prior art is believed to be an article in the following Russian publication: Izv. Akad. Nauk. SSSR, Ser. Khim., 1964 (12), pp. 22-16-77. According to an abstract the article teaches the following: 3-phenyl-1-propene-3-ol heated with 2 moles p-Me C$_6$H$_4$OH in an autoclave at 150° in the presence of 10% catalyst (20% ZnCl$_2$ on Al$_2$O$_3$) gave 80% 1-phenyl-3-(3-methyl-6-hydroxyphenyl)-1-propene.

Another Russian publication, Zh. Org. Khem., 1971, 7 (9), 1960-2 contains the following teachings: phenol condensed with cinnamyl alcohol in the presence of 5 wt.% KO-2 cation-exchange resin gave o- and p-HOC$_6$H$_4$CH$_2$CH:CHPh, 2,6-(PhCH:CH—CH$_2$)$_2$C$_6$H$_3$OH and 2-phenyl-chroman. The major product was the first listed.

Applicants' invention is patentable over the teachings of these references for the following reasons. With regard to the first reference, it does not teach activated alumina as the catalyst. Apparently, the catalyst is zinc chloride on alumina. Since the cresol already has a para-substituent the second substituent can only go in the ortho position. There is nothing in this reference to suggest that the use of activated alumina as the catalyst results in only ortho-substitution.

With regard to the second reference, the catalyst is entirely unlike Applicants'. In addition, the major product is a mixture of ortho and para-substituted phenols.

BRIEF SUMMARY OF THE PRESENT INVENTION

Briefly stated, the present invention is directed to a process for preparing ortho-substituted cinnamyl phenols wherein the process comprises heating at a temperature of about 125° to about 250° C. a mixture of cinnamyl alcohol and phenol in the presence of an effective amount of activated alumina.

DETAILED DESCRIPTION

As is believed to be well-known, the term cinnamyl alcohol refers to a material represented by the formula

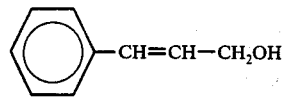

A suitable amount of phenol and cinnamyl alcohol is in the range of about 0.1 to about 5 parts by weight of phenol to alcohol. On the same basis the preferred amount is in the range of about 1 to about 3.

Any activated alumina is suitable for use in our process.

A preferred activated alumina for use in our process is one prepared by the hydrolysis of aluminum alkoxides. The preferred activated alumina has the following properties:

Crystal Structure: α-alumina monohydrate
Surface Area, meters/gram: 230 – 300
Al$_2$O$_3$, weight percent *: 70 – 75
Loose bulk density, grams/liter: 650 – 720

* substantially all of the remainder is water.

A particularly suitable activated alumina is available from Conoco Chemicals Division of Continental Oil Company under the trademark "CATAPAL" ®SB.

A suitable amount of catalyst is in the range of about 1 to about 100 parts by weight of the combined amount of phenol and cinnamyl alcohol. On the same basis the preferred amount of catalyst is about 5 to about 35 parts by weight.

A suitable temperature range for conducting our process is in the range of about 125° to about 250° C. Preferably, the temperature is in the range of about 150° to about 180° C.

Usually the process is conducted in the liquid phase since better results are obtained. Conducting the process in liquid phase may require application of some pressure to keep the reactants in the liquid state. It should be noted that at some temperatures no pressure is required. In any case, the pressure in the process will be in the range of 0 to 70 atmospheres.

The reaction time is in the range of about 0.1 to about 15 hours.

The major product is o-cinnamyl phenol, with the major by-product being 2,6-cinnamyl phenol.

Suitable means for removing the water of reaction should be employed. Knowing this, any person skilled in the art can remove the water of reaction. A typical means of removing the water is by use of toluene as an azeotroping agent and a Dean-Stark trap (or other collecting means).

The desired product can be removed from the reaction mixture by means of fractional distillation.

In the description provided herein we have stated both suitable and preferred ranges. It is to be understood that the process is operable using the suitable ranges but that better results can be obtained using the preferred ranges.

In order to illustrate the nature of the present invention still more clearly the following example will be given. It is to be understood, however, that the invention is not to be limited to the specific conditions or details set forth in this example except insofar as such limitations are specified in the appended claims.

EXAMPLE 1

Phenol (98.2 g), cinnamyl alcohol (94 g), and powered calcined CATAPAL ®SB alumina (21 g) were added to a 500 ml flask with magnetic stirring. Toluene (30 ml) was added to fill a 25 ml Dean-Stark trap plus 5 ml for the reaction flask. The mixture was heated to 170°–180° C. for 1 hour, during which time, 14 ml of water was collected in the trap. No additional water was produced on heating for a longer time. The mixture was cooled and decanted away from the alumina. Analysis of the crude product by gas chromatography showed it to contain 15.6 percent toluene, 17.4 percent phenol, 2.3 percent unknown materials, and 64.7 percent of o-cinnamyl phenol.

Fractional distillation of the crude product using a 4-foot spinning band fractional distillation column gave the following results:

| Cut No. | Bp. at 7mm Hg. | Wt g | Composition |
| --- | --- | --- | --- |
| 1 | 71–74 | 31.8 | Phenol |
| 2 | 74–167 | 2.7 | Phenol + Unknown |
| 3 | 167–200 | 20.5 | Mostly o-Cinnamyl Phenol |
| 4 | 200–204 | 71.5 | o-Cinnamyl Phenol |
| 5 | 204 | 8.5 | o-Cinnamyl Phenol |
| Traps | — | 17.2 | Toluene |
| Residue | — | 15.2 | — |

A sample of material from Cut 4 was examined by Nuclear Magnetic Resonance spectroscopy. The spectrum confirmed that the material was o-cinnamyl phenol.

Thus, having described the invention in detail, it will be understood by those skilled in the art that certain variations and modifications may be made without departing from the spirit and scope of the invention as defined herein and in the appended claims.

We claim:

1. A process for preparing orthosubstituted cinnamyl phenols wherein the process comprises heating an admixture of phenol and cinnamyl alcohol in the liquid phase and at a temperature in the range of about 125° to about 250° C. in the presence of an effective amount of activated alumina, which is $\alpha$ alumina monohydrate, catalyst.

2. The process of claim 1 wherein the phenol and cinnamyl alcohol are present in the range of about 0.1 to about 5 parts by weight of phenol to alcohol.

3. The process of claim 2 wherein the amount of activated alumina catalyst is in the range of about 1 to about 100 parts by weight of the combined amount of phenol and cinnamyl alcohol.

4. The process of claim 3 wherein the reaction time is in the range of about 0.1 to about 15 hours.

5. The process of claim 4 wherein the temperature is in the range of about 150° to about 180° C.

6. The process of claim 5 wherein the phenol and cinnamyl alcohol are present in the range of about 1 to about 3 parts by weight of phenol to alcohol.

7. The process of claim 6 wherein the amount of activated alumina catalyst is in the range of about 5 to about 35 parts by weight of the combined amount of phenol and cinnamyl alcohol.

8. The process of claim 7 wherein the activated alumina has the following additional properties:
surface area, meters/gram:230 – 300
$Al_2O_3$, weight percent:70 – 75
loose bulk density, grams/liter:650 – 720.

* * * * *